United States Patent
Rastegar et al.

(12)
(10) Patent No.: US 6,216,868 B1
(45) Date of Patent: *Apr. 17, 2001

(54) SURGICAL BLADE SYSTEM

(75) Inventors: Jahangir S. Rastegar; Qing Tu, both of Stony Brook, NY (US)

(73) Assignee: Stonybrook Surgical Innovations Inc., Northport, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,130

(22) Filed: Jul. 9, 1999

(51) Int. Cl.[7] .................................................... B65D 83/10
(52) U.S. Cl. ......................... 206/359; 206/356; 206/370; 30/329; 606/167
(58) Field of Search ............................... 30/329, 162, 163, 30/286, 40, 40.1, 40.2, 541; 606/167, 172; 29/239; 206/356, 359, 363, 370

(56) References Cited

U.S. PATENT DOCUMENTS

| | | | |
|---|---|---|---|
| 3,172,316 | * | 3/1965 | Grieshaber . |
| 3,941,243 | | 3/1976 | Yamada . |
| 4,106,620 | * | 8/1978 | Brimmer et al. . |
| 4,120,397 | * | 10/1978 | Neumann . |
| 4,168,777 | * | 9/1979 | Gaskell et al. . |
| 4,180,162 | * | 12/1979 | Magney . |
| 4,270,416 | * | 6/1981 | Thompson . |
| 4,318,473 | * | 3/1982 | Sandel . |
| 4,344,532 | * | 8/1982 | Eldridge, Jr. et al. . |
| 4,378,624 | * | 4/1983 | Klingenberg . |
| 4,386,457 | * | 6/1983 | Coombs . |
| 4,395,807 | | 8/1983 | Eldridge, Jr. et al. . |
| 4,466,539 | | 8/1984 | Frauenhoffer . |
| 4,523,679 | | 6/1985 | Paikoff et al. . |
| 4,730,376 | | 3/1988 | Yamada . |
| 4,746,016 | | 5/1988 | Pollak et al. . |

(List continued on next page.)

FOREIGN PATENT DOCUMENTS

| | | |
|---|---|---|
| 0034949 | 3/1981 | (EP) . |
| 0242035 | 3/1987 | (EP) . |
| 2035186 | 10/1979 | (GB) . |
| 8201058 | 8/1982 | (WO) . |

*Primary Examiner*—Henry J. Recia
*Assistant Examiner*—Anthony S. King
(74) *Attorney, Agent, or Firm*—Robert L. Epstein; Harold James; James & Franklin LLP

(57) ABSTRACT

The handle has a blade mounting portion with a raised boss forming a slot. The blade has a boss receiving recess with a portion defined by an edge. The cartridge has a transparent top so that the presence of a blade within the cartridge can be observed and an opening at one end into which the blade mounting portion of the handle can be inserted. The bottom of the cartridge includes a spring platform with a recess into which the blade is received. The platform is integral with the cartridge bottom and is mounted in cantilever-like fashion, by a living hinge, to permit it to flex. When the top and bottom of the cartridge are assembled, ribs on the top cause the platform to move to a spring loaded position, where the forward end of the handle boss can enter the blade recess. As the blade mounting portion of the handle is inserted further into the cartridge, the flexibility of the platform permits the boss to be fully seated within the recess, mounting the blade on the handle. The blade is then removed from the cartridge by withdrawing the handle. After use, the blade is reinserted into the cartridge. Depression of a pushbutton, accessible from the exterior of the cartridge, permits the boss to be withdrawn from the recess, as the platform flexes, to dismount the blade from the handle. A lid, pivotally attached adjacent the cartridge opening, is adapted to cover the opening to prevent reuse of the used blade.

24 Claims, 6 Drawing Sheets

U.S. PATENT DOCUMENTS

| | | |
|---|---|---|
| 4,903,390 | 2/1990 | Vidal et al. . |
| 4,998,334 | 3/1991 | Pemberton et al. . |
| 5,088,173 | 2/1992 | Kromer et al. . |
| 5,163,553 | 11/1992 | Cantwell et al. . |
| 5,361,902 | 11/1994 | Abiden et al. . |
| 5,406,684 | 4/1995 | Carson . |
| 5,449,068 | 9/1995 | Gharibian . |
| 5,699,908 | 12/1997 | Frye et al. . |
| 5,938,027 * | 8/1999 | Soroff et al. .......................... 206/370 |

* cited by examiner

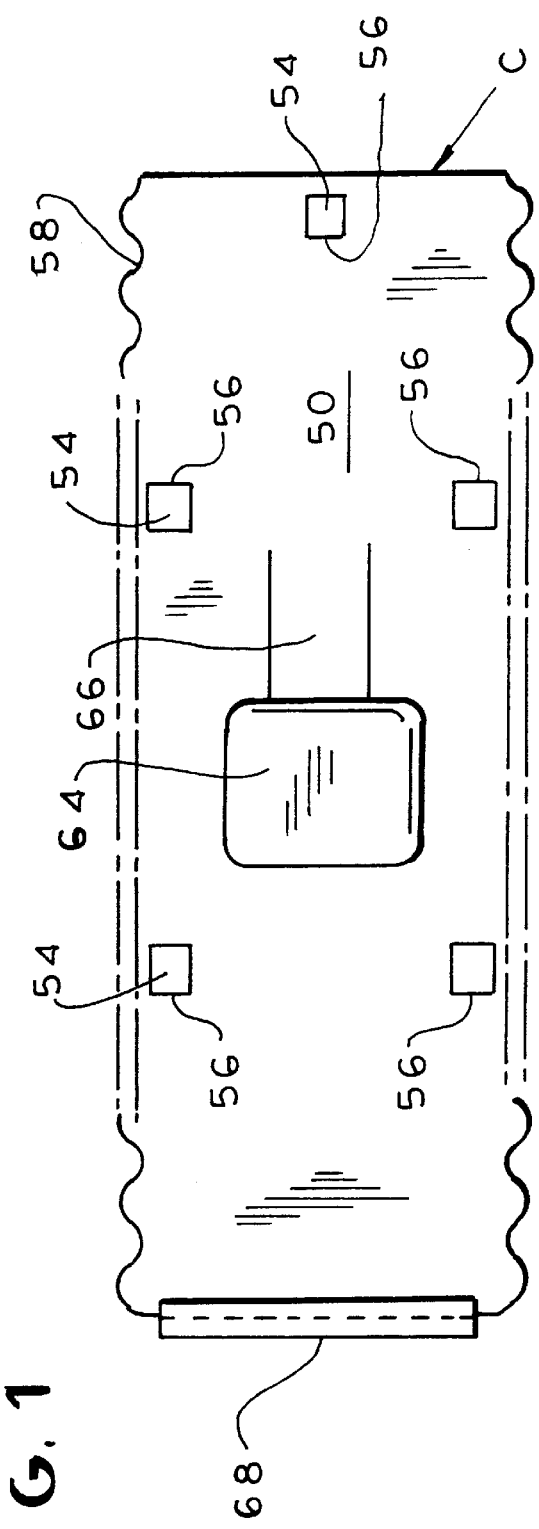
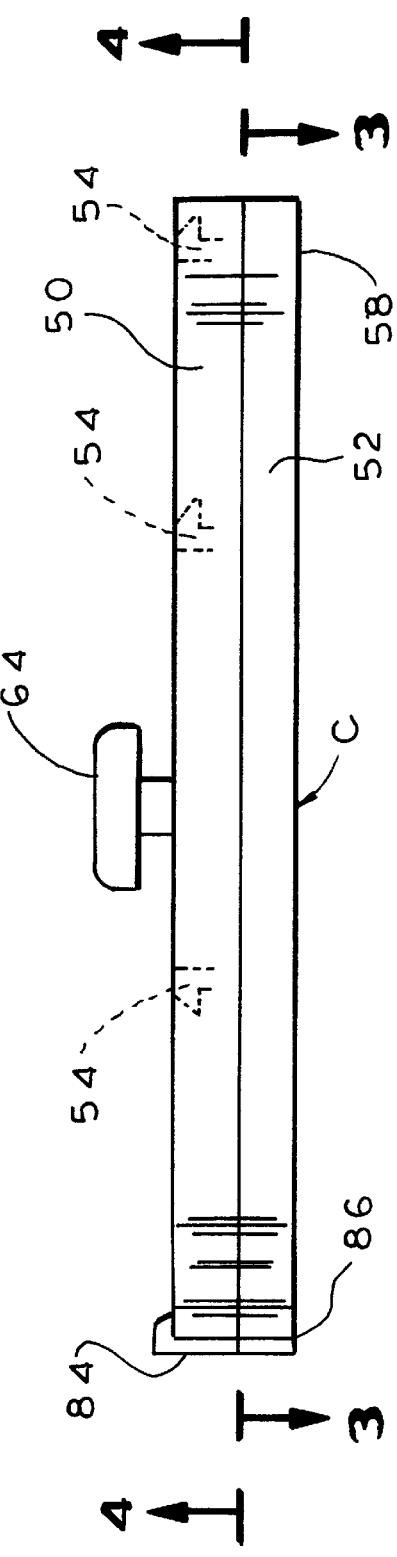

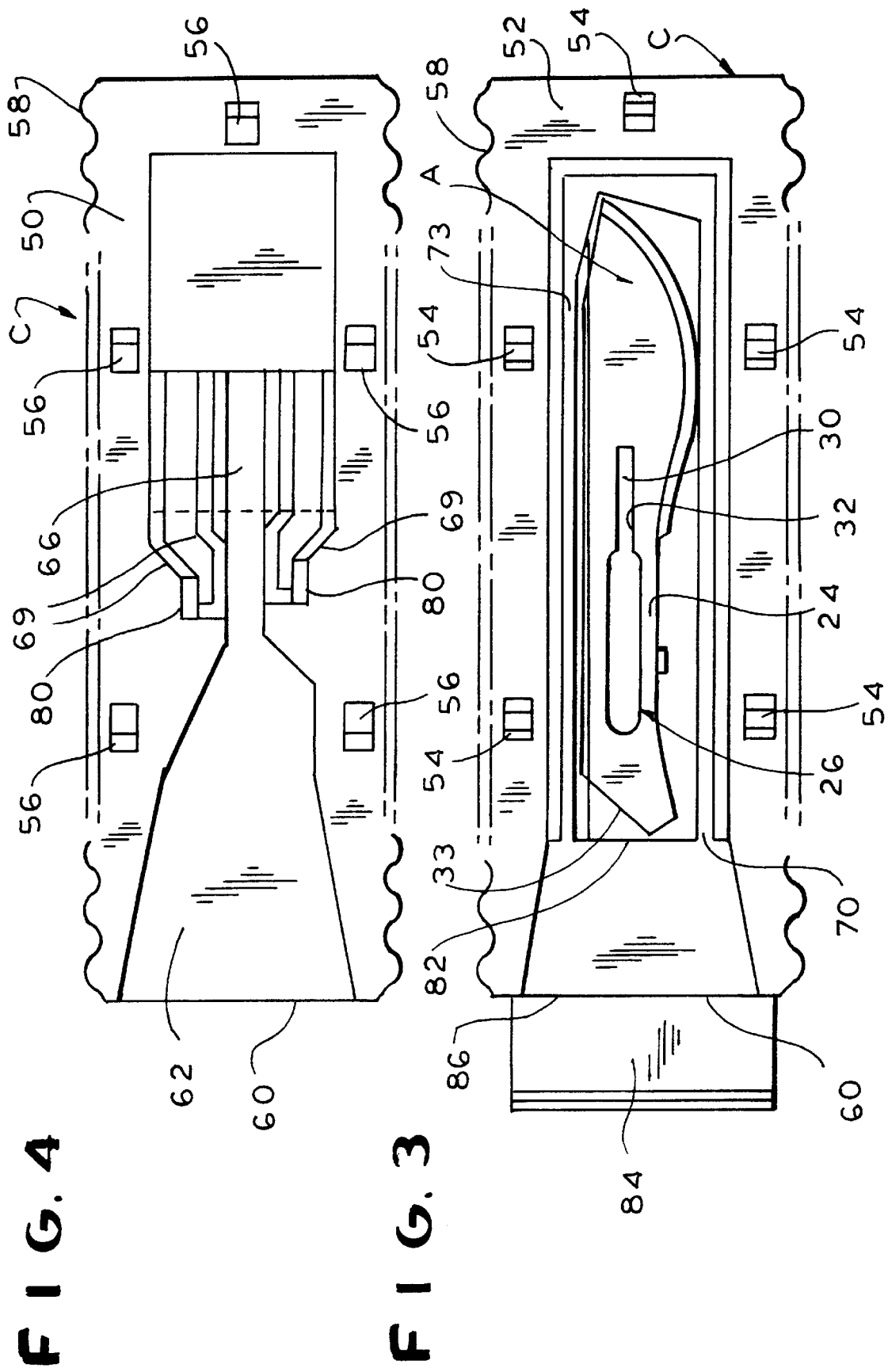

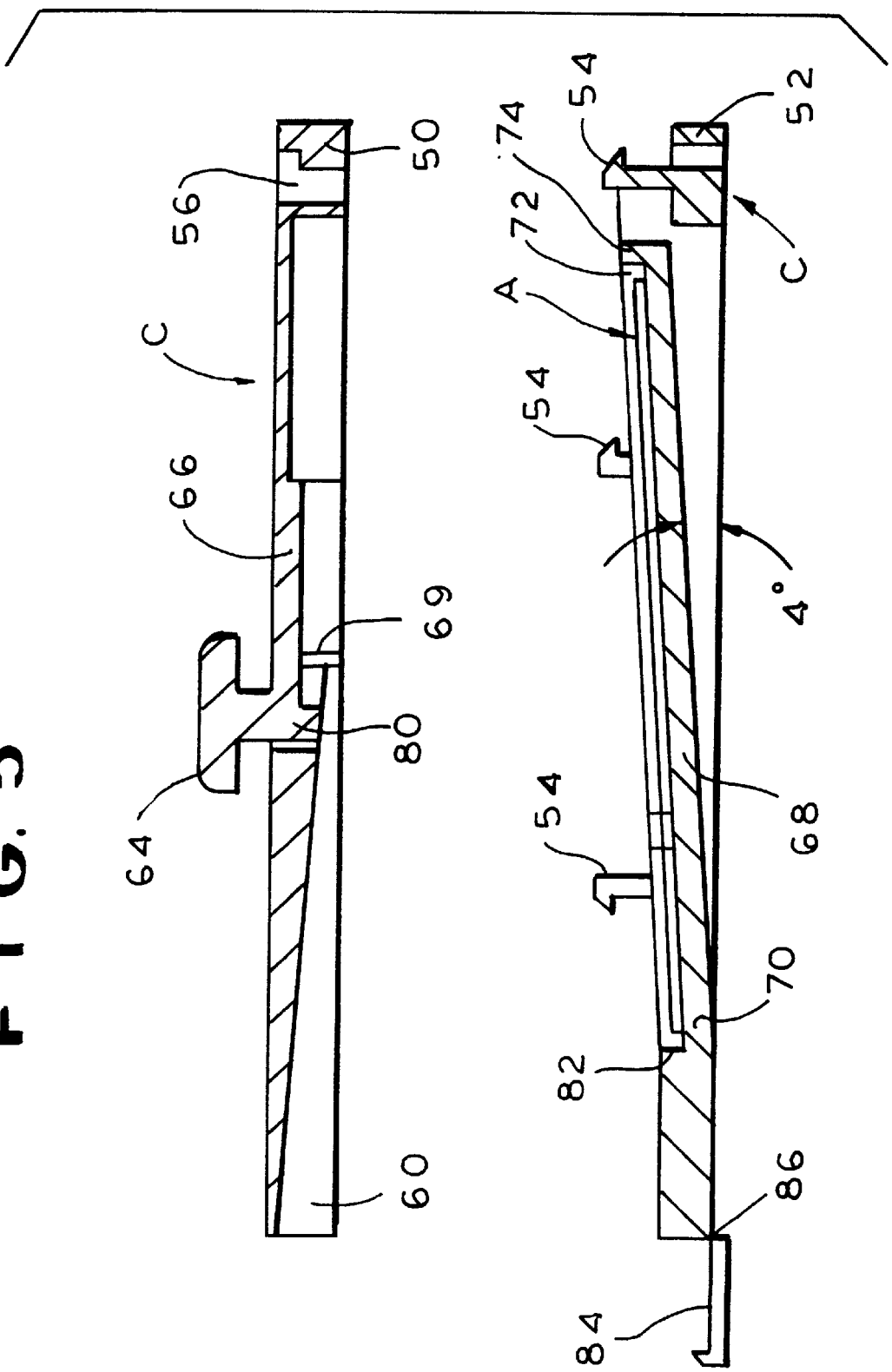

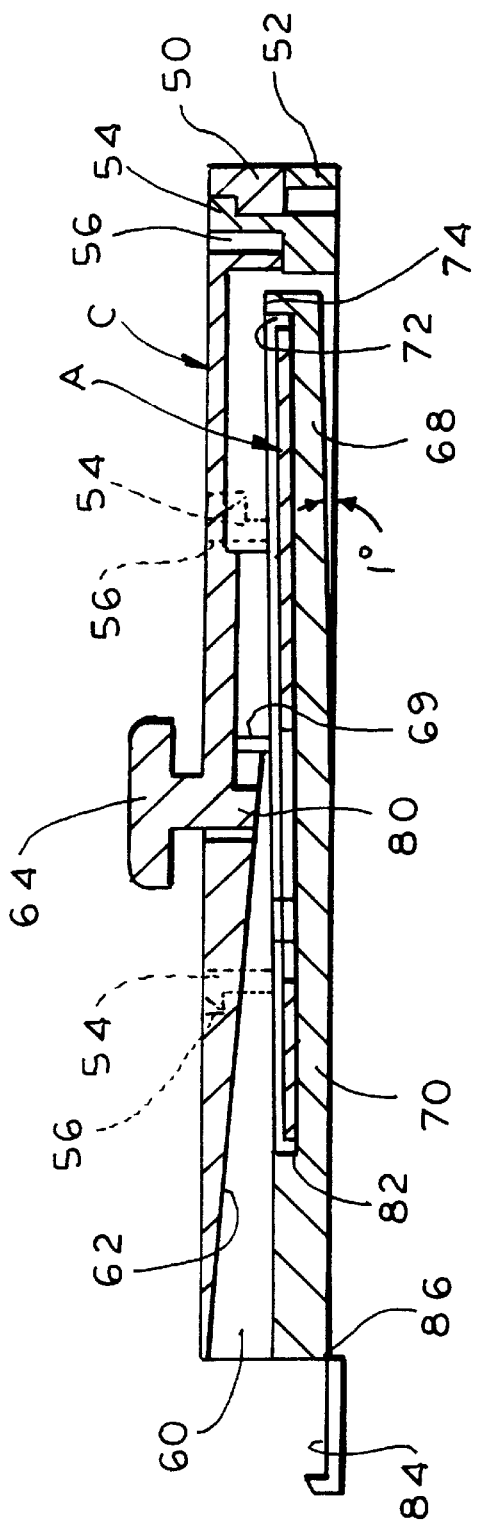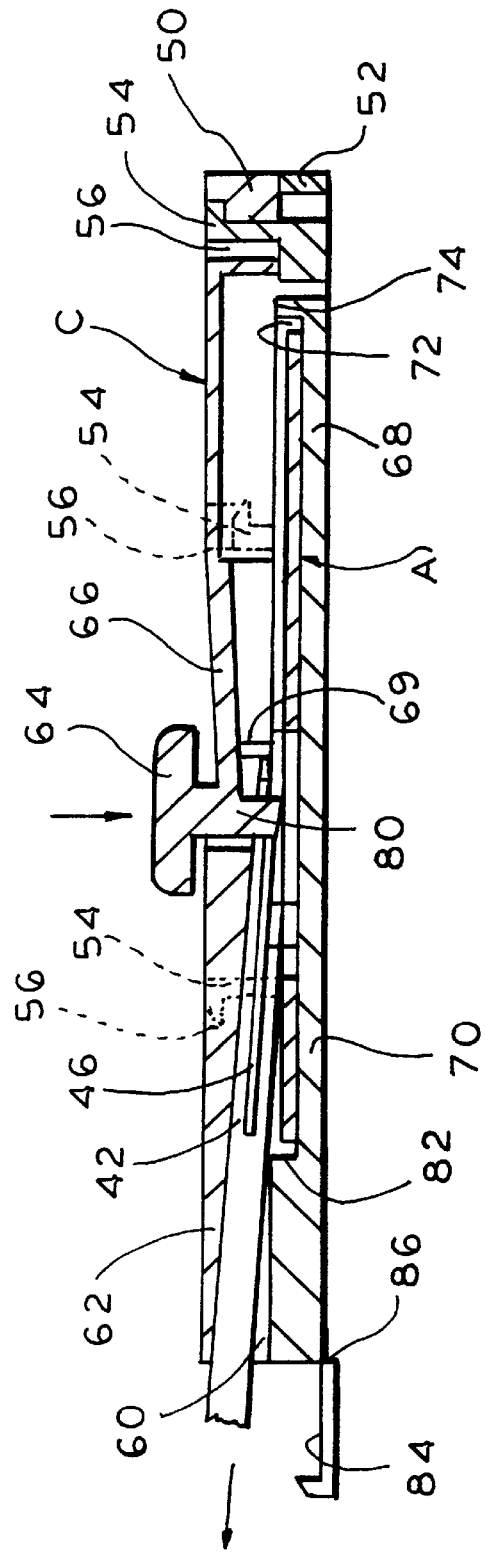

SURGICAL BLADE SYSTEM

The present invention relates to surgical blade dispensing and disposal devices, and, in particular, to a system providing convenient storage, dispensing, and disposal of surgical blades of the type designed to be removeably mounted on a handle by means of a mating elongated recess and boss.

BACKGROUND OF THE INVENTION

It is estimated that worldwide, some eighty five million surgical blades are used annually. Sterilized, stainless steel blades available in many sizes and orientations are designed to be mounted on reusable handles. Most often, the blades are removed from sterile pouches and manually mounted on the handle. After use, contaminated blades are removed from the handle and discarded. Since the mounting and removal of the blade from the handle is done manually, there is potential for cutting and contamination of the personnel who handle the blades.

Many attempts have been made to provide an inexpensive simple apparatus which minimizes the danger of being cut by a contaminated blade, provides for safe disposal and at the same time ensures the sterility of new blades. Providing devices for mounting and removing the blade from the handle without the necessity of touching the blade virtually eliminates the dangers associated with cutaneous injury and exposure to blood which may be infected with HIV or hepatitis.

Typically, commercially available surgical blades have a sharpened tip, a cutting edge portion and a shank portion extending rearwardly therefrom. The shank portion of the blade is provided with an elongated recess which is shaped and adapted to receive a mating elongated boss formed on the forward portion of a handle.

The elongated handle engaging recess of the blade can have widened rear portion and a narrowed forward portion, the widened rear portion initially receiving the engaging boss of the scalpel handle and guiding the boss forward into the narrowed forward portion of the recess. The boss is undercut to form a slot such that the edges of the narrowed forwarded portion of the recess are engaged between scalpel handle and the slot formed by the undercut surface of the boss. When the boss is completely inserted within the blade recess, the rear edge of the blade recess can be snapped over the rear of the engaging boss, thus achieving looking engagement between the blade and the scalpel handle.

In order to remove the blade from a scalpel handle, the rear edge of the blade must be separated from the handle to disengage the rear handle end of the blade recess from the rear end of the boss so that the handle can then be withdrawn until of the undercut boss clears the narrowed forwarded portion of the blade recess, permitting the handle to be cleared of the blade.

A sharp edge is essential in conducting a surgical operation. However, blades tend to lose their edge very quickly so it is common to use several blades during a single surgical procedure. Thus, removal of a used blade from the handle and replacement of the blade with a new sterile blade is a frequent occurrence in the course of a surgical procedure.

In order to reduce the possibility of injury to the handler, various systems to eliminate handling of the blades during mounting and removal of the blades from handles have been developed.

For example, U.S. Pat. No. 3,172,316 to Grieshaber discloses a blade removing tool formed from tubing and having an elongated handle. One end is flattened somewhat so as to provide flat opposed surfaces in which are formed opposed channel-like grooves which function as guide tracks for the boss portion of the scalpel when the tool and the scalpel boss portion are assembled. Extending longitudinally from one flat surface of the flattened end portion of the handle are two spaced apart prongs which are inclined upwardly a slight amount. The space between the prongs is such as to permit the slender boss portion of the scalpel to pass therebetween, the free end of each prong being offset upwardly. handle is moved to the right so that the rear edge of the blade is stripped away from the narrowed forward position of the scalpel handle by engagement against an upstanding blade disengaging projection formed integrally with the floor of the box. The Magney combination dispenser-disposal cartridge can prove to be somewhat ineffective in use resulting in users resorting to manual removal of the blade from scalpel handles.

Other devices include the scalpel blade remover shown in U.S. Pat. No. 4,378,624 to Klingenberg which includes a fixed block in combination with a second moveable block having a slot between such blocks and a tab provided on a moveable block to engage an end of the blade and move it relative to the body of the blade to disengage it from the handle. The blocks are mounted on a supporting surface beneath which a sterile disposal box may be disposed.

U.S. Pat. No. 4,318,473 to Sandel discloses a surgical blade removal and disposal device which operates by inserting a handle with a blade mounted thereon through a guide means so that the rear of the blade is disposed over spaced apart shoulders after which the handle is urged downward tending to bow the blade, thus disengaging the rear of the inserted portion from the rear edge of the blade slot to allow the handle to slide relative to the blade. The blade tends to move with the handle as a result of friction between the blade and the handle until it encounters the front wall of the stop which prevents further movement of the blade rearwardly. One of the problems encountered with the Sandel blade removal device is the severe bend imposed on the blade when it is fit over the spaced apart shoulders to guide the blade to the rear stop. This causes a high degree of friction between the blade slot and the handle boss making removal of the blade very difficult.

U.S. Pat. No. 4,344,532 to Eldridge, Jr., et al. discloses a surgical blade remover having a wedge shaped support member which tapers from its front side to its back side. The support has one or more mutually parallel latitudinal slots open at one end and along their length extending from the front side of the support to its interior. The slots are sized to receive the tang of the blade holder while preventing the blade itself from passing therethrough and the surface of each of the support members bordering the slot is covered with an adhesive which holds the blade in place while the handle is pivoted downward in the slot away from the blade. In certain embodiments, the slots are shown to have modifications contoured to compliment the shape of the blade and/or to provide a notch to receive a portion of the hilt of the blade in order to assist the blade removal.

U.S. Pat. No. 4,120,397 to Neumann discloses a unit for accommodating disposable blade-like articles in which the underside of the blade such as a scalpel blade, slidably engages a resilient tongue-like element which is deflected upwardly. The tongue-like element has mounted thereon means having surfaces which can be pushed against the blade to unseat the rear of the blade away from a boss on the blade handle. Once the tongue-like member is fully depressed thereby deflecting the rear of the blade downwardly, the scalpel handle can be removed, abutting the rear of the blade against the inside surface of a panel, thus unseating the blade from the boss and disassembling the blade from the handle.

U.S. Pat. No. 4,106,620 to Brimmer, et al. shows a surgical blade dispenser and disposal assembly which includes blades individually positioned and supported within the box between a slot in a forward wall and a slot in a rearward wall which holds the blades in such a fashion as to slightly deform them in a lateral curve for receipt of a boss of a surgical blades holder in the elongated slot formed in the body of the blade. The blades can be removed by insertion of the blade bearings handle through the aperture and wedged rearwardly against projecting ears. The handle is then moved laterally to separate the rear of the blade from the boss and remove the handle completely off the blade. This device has proved to be cumbersome and the removal apparatus does not provide for efficient removal of the blades.

U.S. Pat. No. 4,746,016 to Pollak and Blasnik teaches a mechanism which can be used for both mounting and removing a blade having a elongated slot mounting means from a blade handle which has a mounting boss for insertion into the elongated slot. The mechanism includes a handle guide which forms one side of a passageway for insertion of the blade handle. The handle guide has a body portion which is sufficiently flexible to allow deflection of a handle for withdrawal of the boss out of mating relationship with the elongated slot of the blade. Another element of the mechanism is a blade extracting means fixed opposite the handle guide which forms a second side of the passageway. The extracting means has a blade retaining projection arranged adjacent the passageway which can be actuated to prevent withdrawal of a blade from the passageway. The mechanism also includes an actuation means fixed for actuation of a blade extracting means upon deflection of the handle sufficiently to disengage the boss out of a mating relationship with the elongated slot. As consequence, a blade mounted on a handle can be removed when the handle is withdrawn from the passageway, while the extracting means is being actuated.

The Pollack apparatus has proven to be overly complex. Moreover, it requires that the handle be deflected from its original plane to dismount the blade from the handle, a movement which may be awkward to perform. The present system is a significant improvement over the Pollak structure because it is much simpler mechanically and includes a depressible button to easily dismount the blade from the handle.

It is, therefore, a prime object of the present invention to provide a simplified surgical blade system in which sterile surgical blades can be quickly and safely mounted onto a scalpel handle.

It is another object of the invention to provide a surgical blade system which facilitates mounting and dismounting of the blade on a scalpel handle, with a minimum of moving parts.

It is another object of the present invention to provide a blade containing cartridge in which assembly of the parts accurately positions and spring loads the blade retaining platform.

A further object of the present invention is to provide a surgical blade system which prevents reuse of a used blade.

Another object of the invention is to provide a surgical blade system which includes a cartridge with a minimum of components, thereby reducing fabrication and assembly costs.

In accordance with one aspect of the present invention, a surgical blade system is provided comprising a handle having a blade mounting portion with a boss forming a slot. The blade has a boss receiving recess defined by an edge. A cartridge having a body is adapted to removeably retain the blade. The body has an opening adapted to receive the blade mounting portion of the handle. A spring platform having a blade receiving recess is mounted in cantilever fashion to the body. The platform normally retains the blade in a position wherein the boss can enter the blade recess. As a handle is inserted into the opening, the platform flexes to permit the boss to be fully seated within the recess, to mount the blade on the handle.

Means actuatable from the exterior of the cartridge are provided to move the blade relative to the blade mounting portion to dismount the blade from the handle. The actuatable means comprises a pushbutton and a protrusion extending from the pushbutton and adapted to move the blade to a position wherein the boss can be withdrawn from the recess.

The protrusion extends in direction substantially perpendicular to the plane of the platform. The actuatable means preferably comprises first and second spaced protrusions adapted to engage the blade at opposite sides of the boss receiving recess.

The normal position of the platform is at an acute angle with the blade mounting portion of the handle. More specifically, the normal position of the platform is in a plane which forms an acute angle with the plane of the blade mounting portion of the handle.

The platform is integral with the cartridge body, being attached by a "living hinge". It includes means for positioning the blade relative to the platform. The positioning means comprises a surface against which the blade abuts.

A lid is provided. The lid is hingeably attached to the body, adjacent the handle receiving opening.

The cartridge comprises a knurled exterior surface to facilitate handling of the cartridge.

The handle comprises an inclined surface. The blade has a correspondingly inclined mating surface. The cartridge has indicia thereon corresponding to the inclined handle surface.

The cartridge opening is defined by a handle guide surface. The handle guide surface is substantially parallel to the plane of the position of the blade when the platform moves against the spring load.

In accordance with another aspect of the present invention, the surgical blade system includes a handle having a blade mounting surface with a raised boss forming a slot. A blade is provided with a boss receiving recess defined by an edge. A cartridge comprises first and second parts which assemble to removeably retain the blade. The cartridge has an opening adapted to receive the blade mounting portion of the handle. A platform is provided having a blade receiving recess. Means are provided for mounting the platform in cantilever fashion on the second cartridge part. Means are provided on the first cartridge part to cooperate with the platform when the parts are assembled to position the platform to retain the blade in a position where the handle boss can align with the blade recess. Insertion of the handle causes the boss to be received within the recess, to mount the blade on the handle.

The platform is flexible. It is flexed, against a spring load, to permit the boss to be fully received in the blade recess.

The platform mounting means comprises a living hinge. The platform is integral with the second cartridge part.

The cooperating means comprises a rib on the first part. The rib abuts the platform when the parts are assembled.

A lid is provided. The lid is hingeably attached adjacent the cartridge opening.

Pushbutton means, accessible from the exterior of the cartridge, are provided. When actuated, the pushbutton means move the blade to a position wherein the boss can be withdrawn from the recess.

To these and to such other objects which may hereinafter appear, the present invention relates to an improved surgical blade system as st forth in detail in the following specification and recited in the annexed claims, taken together with the accompanying drawings, in which like numerals refer to like parts, and in which:

FIG. 1 is a plan view of the top of the cartridge of the present invention;

FIG. 2 is a side view of the cartridge;

FIG. 3 is a top plan view of the bottom portion of the cartridge taken along line 2—2 of FIG. 2;

FIG. 4 is a bottom plan view of the top part of the cartridge taken along line 4—4 of FIG. 2;

FIG. 5 is an exploded cross-sectional view of the parts of the cartridge with a fresh blade situated in the blade receiving means.

FIG. 6 is a view similar to FIG. 5 but showing the assembled cartridge;

FIG. 9 is a view similar to FIG. 6 showing the blade being dismounted from the handle.

Figure 7:
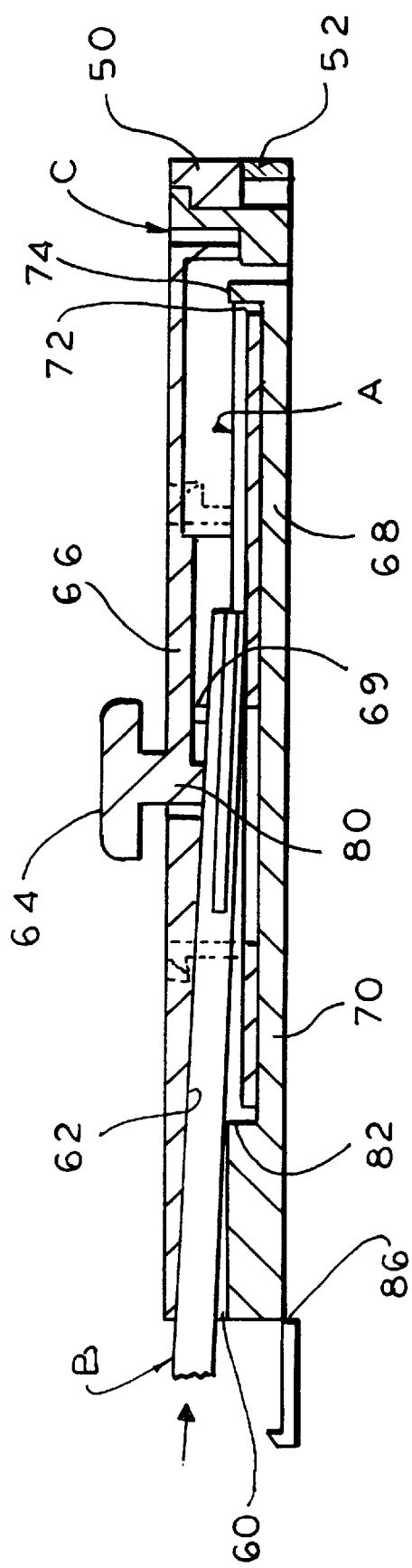
FIG. 7 is a view similar to FIG. 6 showing the handle being inserted into the cartridge.

The surgical blade system of the present invention includes a disposable blade, generally designated A, a handle upon which blade A is adapted to be removeably mounted, generally designated B, and cartridge, generally designated C. Cartridge C retains a blade A in a sterile manner prior to mounting on handle B and receives blade A for safe disposal after it is dismounted from handle B. Cartridge C contains a simple structure which permits mounting and dismounting of the blade on the handle without any direct contact with the blade by the user.

As best seen in FIG. 3, blade A includes a cutting portion 20 with an arcuate cutting edge 22 and a mounting portion 24 with an elongated recess 26. Recess 26 has a larger rear portion 28 and a narrower forward portion 30, defined by an edge 32. The rear edge 33 of blade A is inclined.

Figure 8:
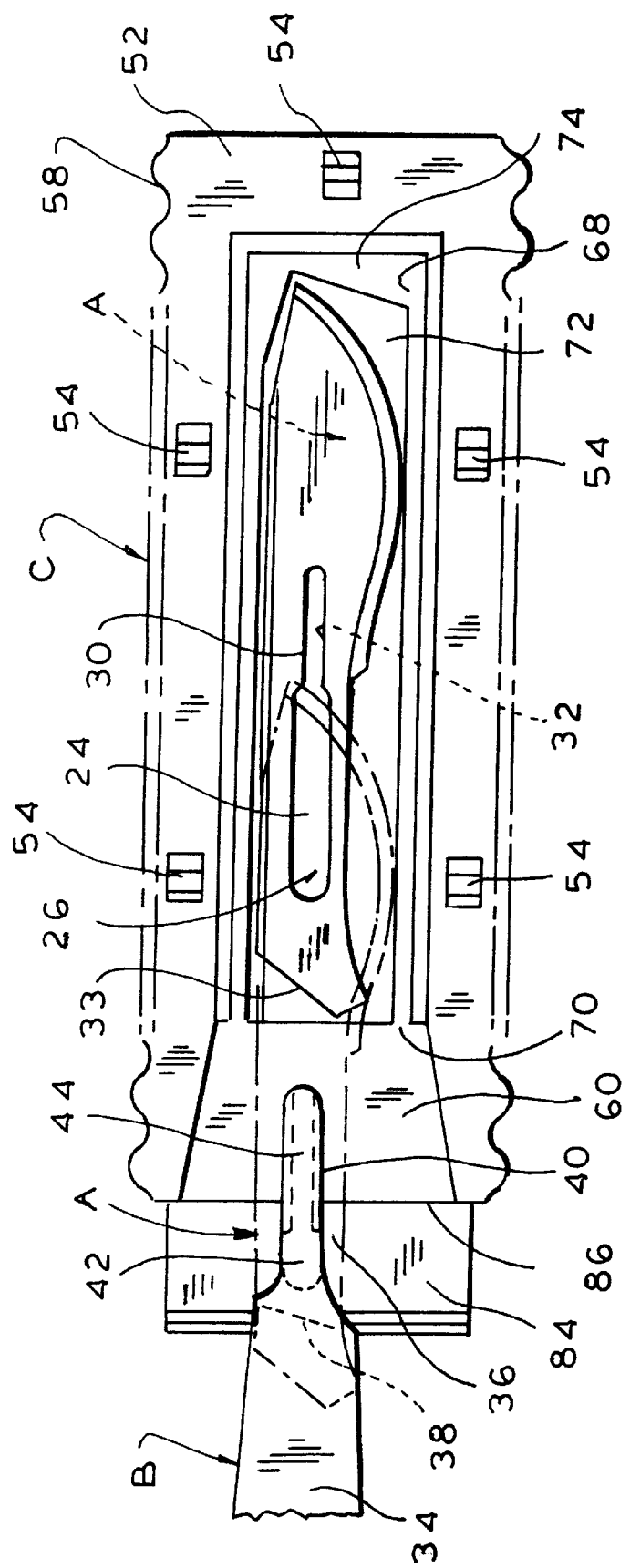
FIG. 8 is a top cross-sectional view showing the handle and blade being reinserted into the cartridge.

As seen in FIG. 8, handle B has a grip portion 34 and a blade mounting portion 36 separated by an inclined surface 38. One surface of blade mounting portion 36 carries a raised boss 40 which has a wider rear portion 42 and a narrower front portion 44. Portion 44 defines, as is best seen in FIG. 9, a slot 46 which is adapted to receive edge 32 of blade A. When mounted on handle B, front portion 44 of the boss will be situated within recess portion 30 and rear portion 42 of the boss will be received within recess portion 28, with the blade and handle coplanar. Inclined surface 33 of blade A will abut surface 38 of handle B.

Figure 10:
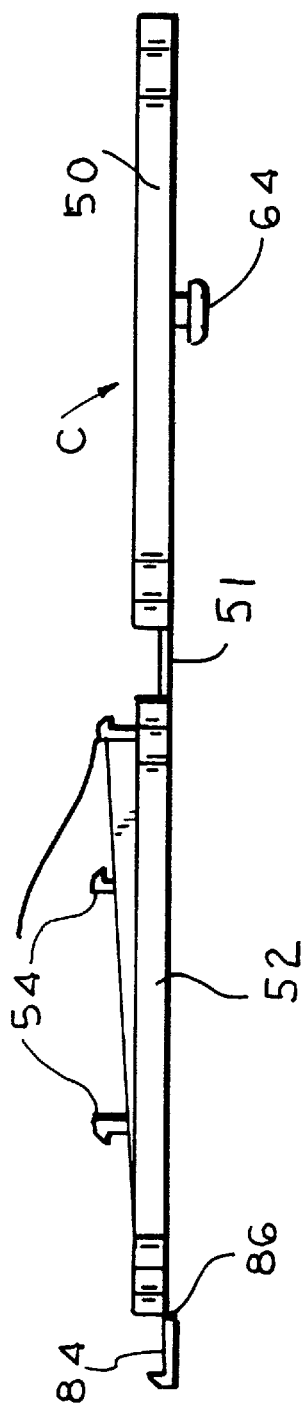
FIG. 10 is a side view of the top and botton of the cartridge as it appears after molding.

Referring now to FIGS. 1 through 5 and 10, cartridge C comprises a plastic housing including a top part 50 and a bottom part 52. Parts 50 and 52 are preferably molded together in a single mold and may be connected by a removable web 51 (FIG. 10). The parts are folded at web 51, into alignment with each other, and are connected together by five upstanding male snaps 54 on part 52 which engage five correspondingly shaped openings 56 on part 50. Parts 50 and 52 are made of medical grade plastic such as polycarbonate or polypropylene. Part 50 is preferably transparent. When assembled, parts 50 and 52 form a hollow enclosure. The enclosure includes an external grip portion having knurled edges 58. It also has a handle entrance opening 60 defined in part by a guide surface 62, which is situated on part 50. A pushbutton 64 is accessible from the exterior of part 50 and is mounted on a "living hinge" 66 integral with part 50.

FIG. 5 shows parts 50, 52 prior to assembly. Part 52 includes an integral spring platform 68 made out of flexible plastic which extends in cantilever-like fashion from part 52 by a "living hinge" so as to be capable of limited pivotal movement about an axis 70, which extends across the cartridge. Prior to assembly, platform 68 in its rest or unloaded position and forms a small acute angle of approximately 4 degrees, with the bottom surface of part 52.

Platform 68 has a blade receiving recess 72 formed on its top surface. Recess 72 is defined in part by a side wall 73 for positioning blade A and an upstanding front lip 74 which acts as a forward stop for the blade. The rear of the blade abuts rear wall 82. Blade A is placed within recess 72 prior to assembly of parts 50 and 52.

Referring to FIG. 6, when parts 50 and 52 are joined together, such that the snaps 54 on part 52 engage openings 56 in part 50, downwardly extending ribs 69 on part 50 cooperate with platform 68 such that platform 68 is flexed or pushed downwardly to a spring loaded position which is almost, but not quite, parallel to the bottom of part 52. In this way, assembly of the parts automatically accurately positions and spring loads the platform to the desired degree. Preferably, the platform in its spring loaded condition is in a plane about 1 degree from the plane of the bottom surface of part 52. However, platform 68 is flexible and can be moved further, upon application of force.

With platform 68 in the spring loaded position (FIG. 6), blade A is in the appropriate position for the forward portion of the handle boss to enter the blade recess. As the handle is inserted in opening 60 (see FIG. 7) and is pushed along guide surface 62, it bears against blade A and edge 32 defining recess portion 30 enters slot 46 defined by the raised boss 40. As the handle continues to move along guide surface 62, platform 68 flexes to a small degree, against the spring load, and the leading portion of the boss 40 can move down the narrow portion 30 of the recess 26 and the following portion 42 of the boss can lodge in the wider portion 28 of the recess, such that the blade and handle are coplanar. The blade is now mounted on the handle. The handle can be withdrawn from the cartridge (FIG. 8) and used.

Pushbutton 64 is used to dismount the blade after it is reinserted into the cartridge. Pushbutton 64 is integral with part 50 and is also made of medical grade plastic.

After the blade is used, the handle with the used blade thereon is reinserted into opening 60 in cartridge C (FIG. 9) until the tip of the blade abuts limiting surface 74 on platform 68. To dismount the blade, pushbutton 64 is depressed. A pair of spaced protrusions 80 extend from the bottom of pushbutton 64, at positions aligned with points on blade A on either side of recess 26. Depressing the pushbutton causes protrusions 80 to engage the surface of blade A and move the rear of the blade out of the plane of handle B so as to partially dismount the used blade from the handle, as platform 68 is flexed against the spring load. The handle can then be withdrawn from the cartridge, while the used blade remains lodged in the cartridge between lip 74 and wall 82. A lid 84, attached adjacent opening 60 by a "living hinge" 86, is placed over the opening. The cartridge, containing the used blade, can then be safely discarded.

It will now be appreciated that the present invention relates to a surgical blade system which permits quick and safe mounting and dismounting of a blade on a handle. The blades are maintained in a sterile condition until used. Contaminated blade can be disposed of without exposing the user.

The system includes a blade retaining cartridge formed of top and bottom parts which, when assembled, position a flexible cantilevered blade retaining platform such that the blade can receive the handle boss. Insertion of the handle into the cartridge causes boss to be received in the blade recess as the platform flexes to mount the blade on the handle. The handle with the blade is withdrawn and the blade used. To dismount the used blade, the handle and blade are reinserted into the cartridge and the pushbutton is depressed. This causes the blade to be moved relative to the handle as the spring platform flexes against the spring loading, permitting the blade to dismount from the handle, so the handle can be withdrawn. A lid is placed over the opening to prevent reuse of the used blade. The contaminated blade remains safely with the cartridge which is then discarded.

While only a single preferred embodiment of the invention as been disclosed herein for purposes of illustration, it is obvious that many variations and modifications could be made thereto. It is intended to cover all of these variations and modifications which fall within the scope of the invention, as defined by the following claims.

We claim:

1. A surgical blade system comprising a handle having a blade mounting portion with a surface with a raised boss, a blade with a boss receiving recess and a cartridge having first and second parts which assemble to form an enclosure for removably retaining said blade, said cartridge having an opening adapted to receive said blade mounting portion of said handle, said second cartridge part having a bottom surface, said cartridge comprising a planar platform in a normal position relative to said second cartridge part bottom surface and having a recess within which said blade is adapted to be received, means for mounting said platform for movement relative to said second cartridge part bottom surface, means extending from said first cartridge part toward said second cartridge part, cooperating with said platform, when said parts are assembled, such that said platform is flexed from said normal position to a first spring loaded position in which said handle boss can align with said blade recess as said handle portion is inserted into said opening, insertion of said handle portion causing said platform to flex from said first spring loaded position to a second spring loaded position, wherein said boss can be received within said recess, to mount said blade on said handle.

2. The system of claim 1 wherein said cooperating means comprises a rib.

3. The system claim 2 wherein said rib abuts said platform when said parts are assembled.

4. The system of claim 1 wherein said platform is integral with said second cartridge part.

5. The system of claim 1 wherein said mounting means comprises a living hinge.

6. The system of claim 1 further comprising pushbutton means actuatable from the exterior of the cartridge to dismount said blade.

7. The system of claim 1 wherein said first spring loaded position is about 1 degree from the plane of said bottom surface.

8. The system of claim 1 wherein said second spring loaded position is substantially parallel with said bottom surface.

9. The system of claim 1 wherein said normal position is approximately 4 degrees from the plane of said bottom surface.

10. The system of claim 1 wherein said cooperating means comprises a plurality of ribs.

11. A surgical blade system comprising a handle having a blade mounting portion with a surface with a raised boss, a blade with a boss receiving recess and a cartridge for removably retaining said blade, having an opening adapted to receive said blade mounting portion of said handle, said cartridge comprising an integral spring platform defining a recess into which said blade is received, a living hinge connecting said platform and said cartridge, said platform normally retaining said blade in a first position wherein said handle boss can enter said recess as said blade mounting portion of said handle is inserted into said opening, said platform being and remaining substantially planar as it is moved relative to said living hinge from said first position to a second position, as said handle portion moves further into said opening, such that said boss can be received within said recess, said blade is mounted on said handle.

12. The system of claim 11 further comprising means actuatable from the exterior of said cartridge to move said blade to a position to dismount said blade from said handle.

13. The system of claim 12 wherein said actuatable means comprises a pushbutton.

14. The system of claim 13 wherein said actuatable means comprises first and second spaced protrusions adapted to engage said blade at points on opposite sides of said boss receiving recess.

15. The system of claim 13 wherein said actuatable means comprises a protrusion extending from said pushbutton, said protrusion moving said blade and flexing said platform when said actuatable means is actuated.

16. The system of claim 15 wherein said protrusion is moved in a direction substantially perpendicular to the plane of said platform.

17. The system of claim 11 wherein said platform comprises means for positioning said blade relative to said platform.

18. The system of claim 17 wherein said positioning means comprises a wall.

19. The system of claim 17 further comprising a surface against which the tip of the blade abuts.

20. The system for claim 11 wherein said cartridge comprises an exterior surface, said exterior surface comprising a knurled surface.

21. The system of claim 11 wherein said cartridge opening is defined by a handle guide surface.

22. The system of claim 11 further comprising a lid for covering said cartridge opening.

23. The system of claim 11 wherein said cartridge has a bottom surface and wherein said first position is in a plane other than the plane of said bottom surface of said cartridge.

24. The system of claim 11 wherein said cartridge has a bottom surface and wherein said second position is substantially in the plane of said bottom surface of said cartridge.

\* \* \* \* \*